United States Patent
Chen et al.

(10) Patent No.: US 8,097,292 B2
(45) Date of Patent: Jan. 17, 2012

(54) METHODS FOR ELECTROSTATIC COATING OF AN ABLUMINAL STENT SURFACE

(75) Inventors: Yung-Ming Chen, Cupertino, CA (US); Fuh-Wei Tang, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 265 days.

(21) Appl. No.: 12/437,292

(22) Filed: May 7, 2009

(65) Prior Publication Data

US 2009/0214756 A1 Aug. 27, 2009

Related U.S. Application Data

(62) Division of application No. 10/833,902, filed on Apr. 27, 2004, now Pat. No. 7,553,377.

(51) Int. Cl.
*B05D 1/04* (2006.01)
(52) U.S. Cl. .................. 427/2.24; 427/2.25; 427/475
(58) Field of Classification Search ................ 427/2.1, 427/2.24, 2.25, 458, 472, 473, 475; 118/500, 118/503
See application file for complete search history.

(56) References Cited

U.S. PATENT DOCUMENTS

| | | | |
|---|---|---|---|
| 4,323,525 A | 4/1982 | Bornat | |
| 4,926,788 A | 5/1990 | Metcalf | |
| 5,470,603 A | 11/1995 | Staniforth et al. | |
| 5,656,080 A | 8/1997 | Staniforth et al. | |
| 5,824,049 A | 10/1998 | Ragheb et al. | |
| 6,010,573 A * | 1/2000 | Bowlin | 118/620 |
| 6,056,993 A * | 5/2000 | Leidner et al. | 427/2.25 |
| 6,096,070 A | 8/2000 | Ragheb et al. | |
| 6,117,479 A | 9/2000 | Hogan et al. | |
| 6,406,738 B1 | 6/2002 | Hogan et al. | |
| 6,669,980 B2 | 12/2003 | Hansen | |
| 2003/0054090 A1 | 3/2003 | Hansen | |
| 2003/0113445 A1 | 6/2003 | Martin | |
| 2003/0138487 A1 | 7/2003 | Hogan et al. | |
| 2003/0143315 A1* | 7/2003 | Pui et al. | 427/2.1 |
| 2003/0185964 A1* | 10/2003 | Weber et al. | 427/2.25 |

FOREIGN PATENT DOCUMENTS

| | | |
|---|---|---|
| EP | 0526606 B1 | 9/1992 |
| EP | 1075838 A2 | 2/2001 |
| EP | 0869847 B1 | 3/2003 |
| EP | 0941072 B1 | 1/2004 |
| GB | 216086 B1 | 1/2000 |
| GB | 2316342 B | 1/2000 |
| GB | 2333975 B | 1/2000 |
| GB | 2336551 B | 1/2000 |
| GB | 2356586 A | 5/2001 |
| GB | 2356587 A | 5/2001 |
| GB | 2333474 B | 6/2001 |
| GB | 2334685 B | 6/2001 |
| GB | 2356585 B | 7/2001 |
| GB | 2374302 A | 8/2001 |
| GB | 2370243 A | 6/2002 |
| GB | 2384199 A | 7/2003 |
| JP | 2919971 | 7/1999 |
| WO | WO 96/35516 | 11/1996 |

(Continued)

*Primary Examiner* — Frederick Parker
(74) *Attorney, Agent, or Firm* — Squire, Sanders & Dempsey (US) LLP

(57) ABSTRACT

A stent mandrel fixture for supporting a stent during the electrostatic application of a coating substance is provided.

16 Claims, 4 Drawing Sheets

FOREIGN PATENT DOCUMENTS

| | | |
|---|---|---|
| WO | WO 98/20863 | 5/1998 |
| WO | WO 01/43727 | 6/2001 |
| WO | WO 01/57144 | 8/2001 |
| WO | WO 02/49771 | 6/2002 |
| WO | WO 02/087550 | 11/2002 |
| WO | WO 03/007918 | 1/2003 |
| WO | WO 03/007919 | 1/2003 |
| WO | WO 03/061841 | 7/2003 |
| WO | WO 03/072084 | 9/2003 |
| WO | WO 03/072086 | 9/2003 |
| WO | WO 2004/017947 | 3/2004 |
| WO | WO 2004/017976 | 3/2004 |
| WO | WO 2004/024339 | 3/2004 |

* cited by examiner

METHODS FOR ELECTROSTATIC COATING OF AN ABLUMINAL STENT SURFACE

This application is a divisional application of U.S. application Ser. No. 10/833,902, filed Apr. 27, 2004, now U.S. Pat. No. 7,553,377, which is incorporated herein by reference in its entirety.

TECHNICAL FIELD

This invention relates to apparatus and method for electrostatic coating of stents, more specifically to a stent mandrel fixture used during the electrostatic coating process.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend can be applied to the stent by immersing the stent in the composition or by spraying the composition onto the stent. The solvent is allowed to evaporate, leaving on the surfaces a coating of the polymer and the therapeutic substance impregnated in the polymer.

The dipping or spraying of the composition onto the stent can result in a complete coverage of all stent surfaces, i.e., both luminal (inner) and abluminal (outer) surfaces, with a coating. However, from a therapeutic standpoint, drugs need only be released from the abluminal stent surface, and possibly the sidewalls. Moreover, having a coating on the luminal surface of the stent can have a detrimental impact on the stent's deliverability as well as the coating's mechanical integrity. A polymeric coating can increase the coefficient of friction between the stent and the delivery balloon. Additionally, some polymers have a "sticky" or "tacky" nature. If the polymeric material either increases the coefficient of friction or adherers to the catheter balloon, the effective release of the stent from the balloon upon deflation can be compromised. Severe coating damage at the luminal side of the stent may occur post-deployment, which can result in a thrombogenic surface. Accordingly, there is a need to eliminate or minimize the amount of coating that is applied to the inner surface of the stent. Reducing or eliminating the polymer from the stent luminal surface also means a reduction in total polymer load, which will minimize the material-vessel interaction and is therefore a desirable goal for optimizing long-term biocompatibility of the device.

A method for preventing the composition from being applied to the inner surface of the stent is by placing the stent over a mandrel that fittingly mates within the inner diameter of the stent. A tubing can be inserted within the stent such that the outer surface of the tubing is in contact with the inner surface of the stent. With the use of such mandrels, some incidental composition can seep into the gaps or spaces between the surfaces of the mandrel and the stent, especially if the coating composition includes high surface tension (or low wettability) solvents. Moreover, a tubular mandrel that makes contact with the inner surface of the stent can cause coating defects. A high degree of surface contact between the stent and the supporting apparatus can provide regions in which the liquid composition can flow, wick, and/or collect as the composition is applied to the stent. As the solvent evaporates, the excess composition hardens to form excess coating at and around the contact points between the stent and the support apparatus, which may prevent removal of the stent from the supporting apparatus. Further, upon removal of the coated stent from the support apparatus, the excess coating may stick to the apparatus, thereby removing some of the coating from the stent and leaving bare areas. In some situations, the excess coating may stick to the stent, thereby leaving excess coating composition as clumps or pools on the struts or webbing between the struts. Accordingly, there is a tradeoff when the inner surface of the stent is masked in that coating defects such as webbing, pools and/or clumps can be formed on the stent.

In addition to the above mentioned drawbacks, other disadvantages associated with dip and spray coating methods include lack of uniformity of the produced coating as well as product waste. The intricate geometry of the stent presents a great degree of challenges for applying a coating material on a stent. Dip coating application tends to provide uneven coatings and droplet agglomeration caused by spray atomization process can produce uneven thickness profiles. Moreover, a very low percentage of the coating solution that is sprayed to coat the stent is actually deposited on the surfaces of the device. A majority of the sprayed solution is wasted in both application methods.

To achieve better coating uniformity and less waste, electrostatic coating deposition has been proposed. Examples in patent literature covering electrostatic deposition include U.S. Pat. Nos. 5,824,049 and 6,096,070. Briefly, referring to FIG. 1, for electro-deposition or electrostatic spraying, a stent 100 is grounded and gas is used to atomize the coating solution into droplets 110 as the coating solution is discharged out from a nozzle 120. The droplets 110 are then electrically charged by passing through an electrical field created by a ring electrode 130 which is in electrical communication with a voltage source 140. The charged particles are attracted to the grounded metallic stent. An alternative design for coating a stent with an electrically charged solution is disclosed by U.S. Pat. No. 6,669,980. U.S. Pat. No. 6,669,980 teaches a chamber that that contains a coating formulation that is connected to a nozzle apparatus. The coating formulation in the chamber is electrically charged. Droplets of electrically charged coating formulation are created and dispensed through the nozzle and are deposited on the grounded stent. Stents coated with electrostatic technique have many advantages over dipping and spraying methodology, including, but not limited to, improved transfer efficiency (reduction of drug and/or polymer waste), high drug recovery on the stent due to elimination of re-bounce of the coating solution off of the stent, and better coating uniformity, and a faster coating process. Formation of a coating layer on the inner surface of the stent is not, however, eliminated with the used of electrostatic deposition. With the use of mandrels that ground the stent and provide for a tight fit between the stent and the mandrel, formation of coating defects such as webbing, pooling and clumping remain a problem. If a space is provided between the mandrel and the stent, such that there is only minimal contact to ground the stent, the spraying can still penetrated into the gaps between the stent struts and coat the inner surface of the stent. Conventional stent geometry does not provide for a good Faraday cage due to the interspace between the struts of the stent. As illustrated by FIG. 2, electric field lines can penetrated into the opening between the struts and deposit a coating on the inner surface of the stent. This is known as the "wrap around" effect. Charged particles are not only disposed on the outer surface of the stent, but also are wrapped around each strut and are attracted to the inner surface of the stent.

Accordingly, what is needed is an apparatus and method that allows for electro-deposition or electrostatic spraying of a stent while eliminating or minimizing the wrap around effect.

SUMMARY

In accordance with one embodiment of the invention a stent mandrel fixture to support a stent during application of a charged coating substance to the stent is provided, comprising a first mandrel component in conductive contact with the stent and a second mandrel component positioned at least partially within a bore of the stent, the second mandrel component being made from a nonconductive material, being coated with a nonconductive material or having a nonconductive sleeve disposed thereon. The first mandrel component can provide for a charge differential to the stent relative to the coating substance. The nonconductive material or the sleeve is capable of collecting a charge of the same polarity as the coating substance. In some embodiments, the coating substance includes a conductive solvent.

In accordance with another embodiment, a fixture to support a stent during application of a charged coating substance to the stent is provided, comprising a mandrel component extending at least partially through a longitudinal bore of the stent, the mandrel component being configured to minimize or eliminate the wrap around effect of the charged coating substance around the stent struts to prevent or reduce the amount of coating substance applied to an inner side of the stent. The mandrel component includes an element configured to collect charged particles applied to the component. The mandrel component includes an element configured to repel charged particles applied to the component. The fixture can also include a second mandrel component in electrical communication with the stent. The second mandrel component is for applying a charge to the stent and/or to ground the stent.

In accordance with another embodiment, an electrostatic spray coating apparatus for electrostatic application of a substance to a stent is provided comprising a stent mandrel fixture having a first mandrel component in conductive contact with the stent, a second mandrel component positioned at least partially within a bore of the stent, the second mandrel component configured to repel charged particles so as to eliminate any, or reduce the amount of, coating substance applied to an inner side of the stent, a coating substance dispenser positioned at a distance away from the stent, and a power source to charge the coating substance.

In accordance with other embodiments, methods of coating a stent with a substance are provided. The method can include supporting a stent on a mandrel, charging the coating substance, applying the coating substance to the stent, and applying a charge to the stent and/or grounding the stent via the first mandrel component. In one embodiment, the method comprising applying charged particles to a part of the mandrel prior the applying the coating substance to the stent.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

It is believed that the embodiments of the invention can provide for a uniform coating, prevent excess waste associated with conventional dip and spray coating processes, and prevent a coating from being formed on the inner surface of the stent or reduce the amount of coating that is formed on the inner surface of the stent. This reduces the total polymer load on a stent, thereby improving long-term biocompatibility and ensuring that most of the coating is on the abluminal surface where it provides the most benefit. Further, problematic interactions between a delivery mechanism (e.g., delivery balloon) and the stent luminal surface are eradicated, thereby increasing the ease of stent deliverability.

Figure 1:
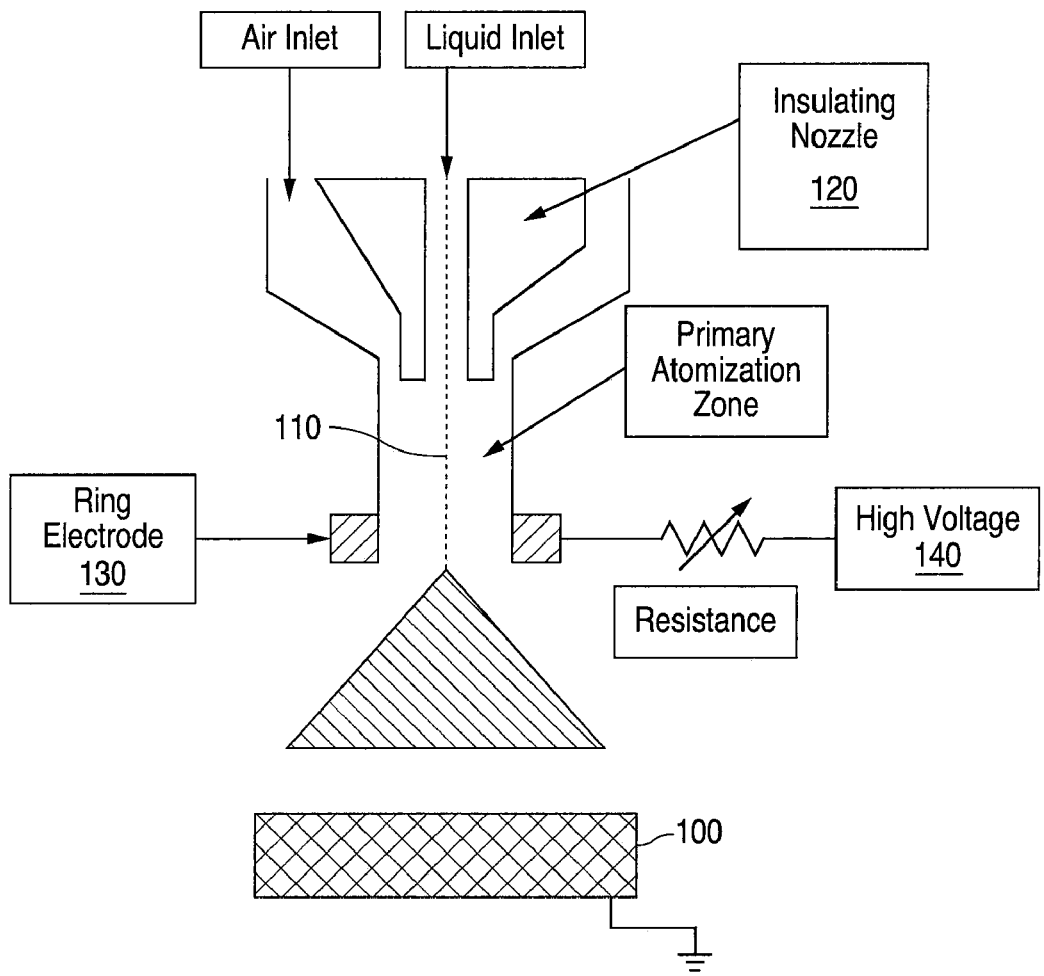
FIG. 1 is a block diagram illustrating an electrostatic spray coating system.
Figure 2:
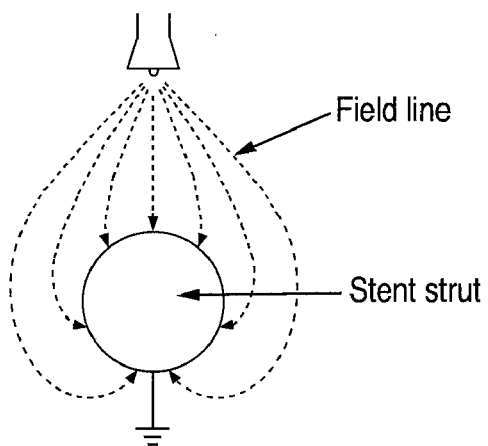
FIG. 2 illustrates the wrap around effect on a stent strut.
Figure 3:
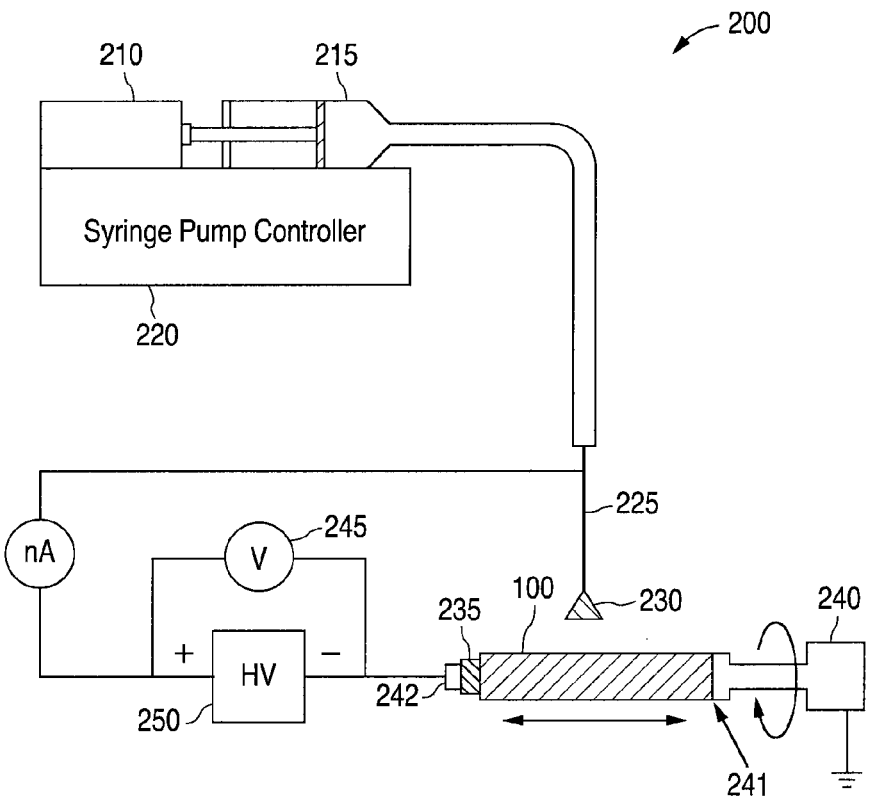
FIG. 3 is a block diagram illustrating an electrostatic spray coating system.

FIG. 3 illustrates an electrostatic spray coating system 200. The system 200 includes a syringe pump controller 220 communicatively coupled to a pump 210 (e.g., a Harvard syringe pump model 11) that pumps a syringe 215 holding a composition. As discussed further below, the composition can include any type of a coating material such as solvent(s), polymer(s), therapeutic substance(s) or any one or combination of these. The syringe 215 dispenses the composition onto the stent 100 via a metallic dispensing tip, hypotube 225 or other dispenser that is coupled to the syringe 215.

Figure 4A:
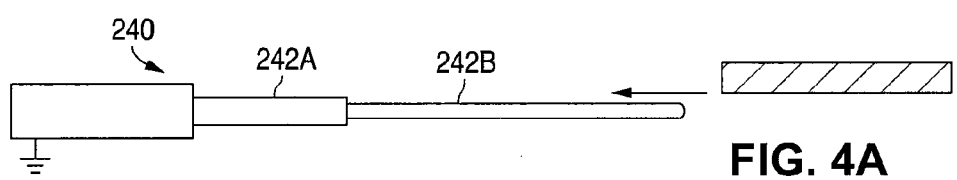
FIGS. 4A, 4B and 4C illustrate a mandrel in accordance with one embodiment of the invention.
Figure 4B:
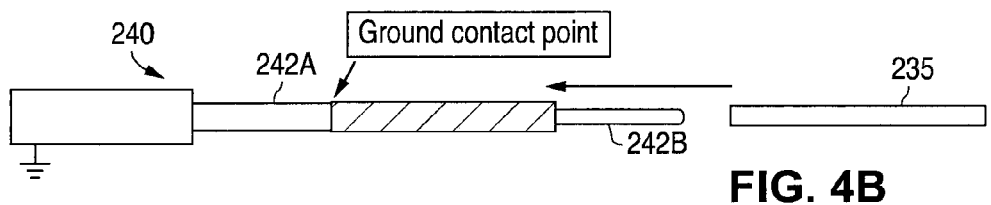
Figure 4C:
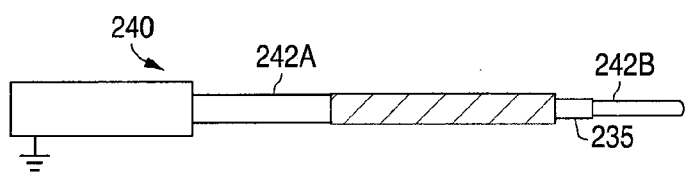

The stent 100 is mounted on a stent mandrel fixture 240 that can provide translational and rotational movement of the stent 100 during a coating process. The stent 100 can be located, for example, approximately 20-25 mm downstream from the hypotube 225. As illustrated by FIGS. 4A, 4B and 4C, the mandrel fixture 240 includes a mandrel arm 242 that can extend partially or all the way through the bore of the stent 100. The mandrel arm 242 includes a larger first diameter section 242A extending to a smaller second diameter section 242B. The larger diameter section 242A should be of sufficient size to allow one end of the stent 100 to be crimped thereon or to allow for a friction fit within the one end of the stent 100. The fitting should be tight enough that the stent 100 is supported over the smaller diameter section 242B without making contact with section 242B. In other words, a gap is disposed between the outer surface of the smaller diameter section 242B and the inner surface of the stent 100. The larger diameter section 242A should be made from a conductive material, such as a metal, so as to allow for charge transmission from the stent 100. In one embodiment, the smaller diameter section 242B can be made from a non-conductive material such as a rubber, plastic, polymer or ceramic material. Alternative, the smaller diameter section 242B can also be made of a conductive material or other material and insulated with a sleeve 235 made from a non-conductive material (also referred to interchangeably as an insulating material) such as rubber, plastic, polymer or ceramic material. Particular examples include pellethane, nylon, Teflon, polyvinylchloride (PVC), etc. Non-conductive, insulator or insulating refers to the ability of a material to prevent the flow of electric current between or among points. Insulation resistance can be measured in megaohms per stated volume or area. In some embodiments, insulator, insulating or non-conductive means less or significantly less conductive that the segment of the mandrel fixture 240 that grounds and/or applies a charge to the stent, so long as the insulating or non-conductive component(s) of the fixture 240 reduces or prevents the wrap around effect for eliminating or minimizing the formation of the coating on the inner surface of a stent.

In yet another embodiment, smaller diameter section 242B can be coated with an insulating material. As used herein, insulating sleeve and coating, although very different in form, will be used interchangeably for brevity. The same concepts that are disclosed with the sleeve apply equally with the use of a coating. With the use of the sleeve 235, the smaller diameter section 242B must of sufficiently small diameter so as to allow for the gap to exist between the sleeve 235 and the inner surface of the stent 100. The insulating sleeve 235 can have a length equal to at least about the length of the stent 100. Shorter length sleeves can be used to provide for the wrap around effect at an end of the stent. This may be suitable if it is desired to provide for more drug at one end of the stent. The sleeve 235 can be in tubular form. The sleeve 235 can also be patterned so as to provide some areas where the conductive mandrel 240 is exposed so as to selectively be able to coat designated areas of the inner surface of the stent 100. This may be desirable in order to provide some degree of friction or adhesiveness between a balloon and the stent. In one embodiment of the invention, the sleeve 235 has an inner diameter of about 0.042 inches and an outer diameter of about 0.054 inches. The thickness of the sleeve 235 depends on the material used. The gap or spacing between the luminal surface of the stent 100 and the outer diameter of the sleeve 235 (or the outer surface of a nonconductive smaller diameter section 252B or a coating) can be about 0.005 inches, for example.

Figure 5A:
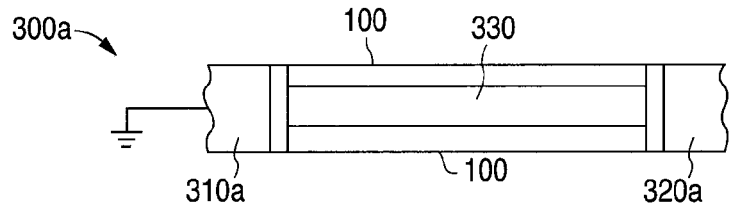
FIGS. 5A, 5B and 5C illustrate the mandrel in accordance with various other embodiments of the invention.

Referring to FIG. 5A, in accordance with another embodiment, a mandrel fixture 300a can include a support member 310a that engages or is disposed in one end of the stent 100 and a lock member 320a that engages or is disposed in the opposing end of the stent 100. The support member 310a and the lock member 320a can be coupled together by a mandrel arm 330 that extends through the longitudinal bore of the stent 100. The arm 330 can be permanently coupled to the support member 310a and releasable coupled to the lock member 320a, such as by a screw fit or a friction fit. The support member 310a and/or lock member 320a can be in conductive communication with the stent 100. In one embodiment, the mandrel arm 330 can be made from a non-conductive material or alternatively the sleeve 235 can be disposed over the arm 330. Again, a coating can be used in lieu of the sleeve 235. In some embodiments, one of the support member 310a and the lock member 320a can also be made from a non-conductive material, have an insulating sleeve disposed thereon or be coating with an insulating material.

Figure 5B:
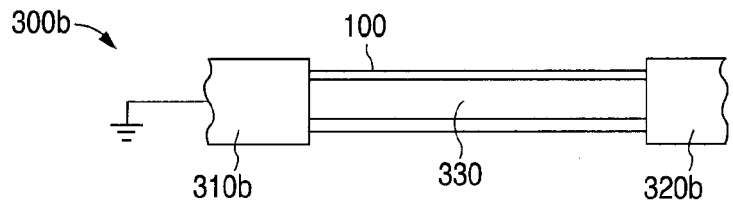

With the use of the mandrel fixtures of FIGS. 4A, 4B, 4C, it is possible that some coating defects can be formed in the areas of the end ring segment or segments of the stent 100 that are disposed over that the mandrel section 242A. The coating composition can be equally attracted to the mandrel and form areas of coating conglomeration between the stent struts that are positioned over section 242A. This would be equally true for the embodiment of FIG. 5A as there are now overlapping areas at both ends of the stent 100. To minimize coating defects, the stent 100 can be locked between two surfaces as illustrated in the mandrel fixture 300b of FIG. 5B. The support member 310b and the lock member 320b of FIG. 5B provide ends that are larger than the diameter of the stent 100—as positioned on the fixture—so as to allow the stent 100 to be pinched there between. In some embodiments, the stent 100 can be threaded over the arm 330 and placed against the support member 310b. The lock member 320b is then screwed or friction fitted onto the arm 330 and moved incrementally closer to the support member 310b so as to gently pinch the stent 100 there between. A certain degree of manual adjustment may be necessary to center the stent 100. The support member 310b and/or the lock member 320b can be made from a conductive material so as to ground the stent 100. If only one of the members 310b or 320b is in electrical communication with the stent 100, the other member as well as the arm 300 can be made from a non-conductive material or can be insulated with a sleeve or a coating.

Figure 5C:
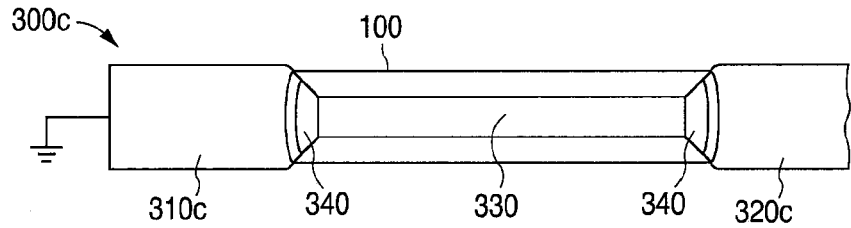

In another embodiment of the invention, a mandrel fixture 300c, as shown in FIG. 5C, includes a support member 310c and/or a lock member 320c that can have a coning end portion 340 that penetrates partially into the stent 100 ends and allows the stent 100 to rest thereon. With this embodiment, the necessity of manually centering the stent 100 is eliminated. In one embodiment, at least one of the coning end sections 340 can be made from a conductive material. The other end 340 as well as the arm 330 can be made from a non-conductive material, or can be insulated with a sleeve or a coating. In some embodiments, a segment of a tip of the conductive coning end or ends 340 that is disposed within the stent 100 can be made from a nonconductive material or can be insulated by a sleeve or a coating. In some embodiments, the tip 340 should be large enough so as to allow for nominal conductive contact between the fixture 300c and the stent 100. The wrap around effect, therefore is further reduced at the stent 100 ends.

In some embodiments, the non-conductive or insulated segment of the mandrel fixture 240 should expand across and beyond the length of the stent or a majority of the length of the stent 100 so as to eliminate or minimize any coating from being formed on the inner surface of the stent 100. However, as discussed above, the coverage of the non-conductive or insulating segment of the mandrel fixture 240 can be adjusted so as to allow for some coating to be formed on the inner surface of the stent 100. In some embodiments the total length of the inner surface that is protected from the wrap around effect can be greater than 99%, 95%, 90%, 80%, 70%, 60% or 50%.

Referring back to FIG. 3, a power source 245 is coupled to a high voltage transformer 250 that converts voltage from the power source 245 to a high voltage (e.g., up to 20 kV), which is then applied to the hypotube 225. The high voltage ionizes the composition into atomized ionized (e.g., negatively or positively charged) droplets in a spray 230 without the need for atomizing air. However, in an embodiment of the invention, the hypotube 225 may be replaced by an air-assisted atomization nozzle, which connects to an atomizing air source to provide atomizing air to assist in atomization of the composition. The atomization can be external or internal.

Atomization of the composition using electrospray is governed by the Rayleigh Limit, which holds that droplets can be broken apart if the charge of the droplets exceeds the surface tension of the droplets. Specifically, the maximum charge of a droplet is related to the surface tension as follows:

$$Q=8\pi\sqrt{\epsilon_o\gamma R^3}$$

wherein $\epsilon_o$ is the permittivity of a vacuum or medium in which the droplets are atomized; $\gamma$ is the surface tension of the liquid the droplet is made of, and R is radius of the droplet. Accordingly, a sufficiently high voltage must be applied to the composition to impart a high enough charge to overcome the surface tension.

The stent 100 is in electrical contact with the stent mandrel fixture 240 at point 241 (for FIG. 4, at an end of the stent 100) such that any charge applied to the stent 100 is conducted to the mandrel 240. The stent mandrel fixture 240 may be grounded and/or electrically connected to a power source 245 via one end of the mandrel 242, as will be discussed further below, to form a complete circuit. Therefore, the stent 100 does not collect charge having the same polarity as the atomized ionized droplets of the spray 230. The insulating sleeve 235 (or the coating or the non-conductive segment of the mandrel fixture 240) is an insulator and therefore does not conduct charge. Any charge dispensed onto the sleeve 235 (e.g., from the spray 230) will therefore build up and not be transmitted.

During a coating process, the hypotube 225 dispenses the composition as an ionized and atomized spray 230 onto the stent 100, which is rotated and translated to ensure that the abluminal surface of the stent 100 is fully and uniformly coated. Charge from the ionized spray 230 does not build up on the stent 100. In an embodiment of the invention, the stent mandrel fixture 240 can be coupled to the power source 245, which will therefore pull any charge from the stent 100 thereby leaving the stent 100 neutrally charged or having a charge opposite of the ionized spray 230 (e.g., having a positive charge). If a charge having the same polarity as the ionized spray 230 were to build up on the stent 100, the stent 100 would repel the ionized spray 230, thereby preventing coating of any surface of the stent 100. In contrast, the insulating sleeve 235 does build a charge having the same polarity as the ionized spray 230. Accordingly, the insulating sleeve 235 will repel the atomized ionized spray 230 from the interior diameter of the stent 100. The wrap around effect is therefore reduced or eliminated.

The components of the coating substance or composition can include a solvent or a solvent system comprising multiple solvents; a polymer or a combination of polymers; and/or a therapeutic substance or a drug or a combination of drugs. Representative examples of polymers that can be used to coat a stent or medical device include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof. Solvents should have a high enough conductivity to enable ionization of the composition if the polymer or therapeutic substance is not conductive. For example, acetone and ethanol have sufficient conductivities of $8\times10^{-6}$ and $\sim10^{-5}$ siemen/m, respectively.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Figure 6:
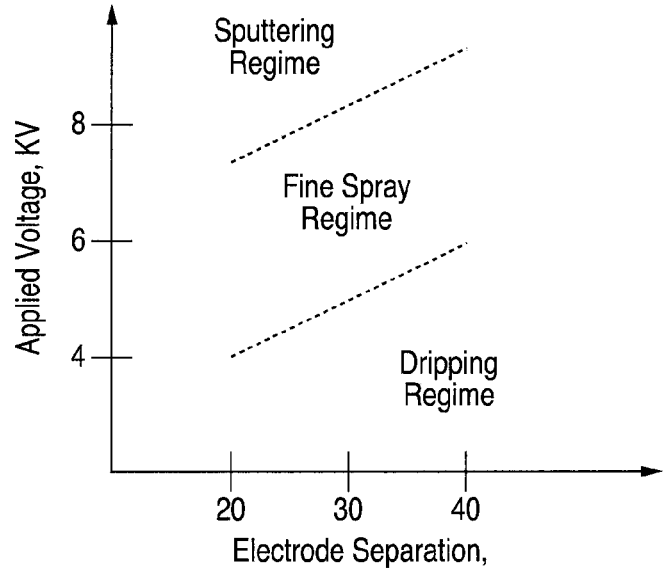
FIG. 6 is chart illustrating spray regimes as a function of applied voltage and electrode separation.
Figure 7:
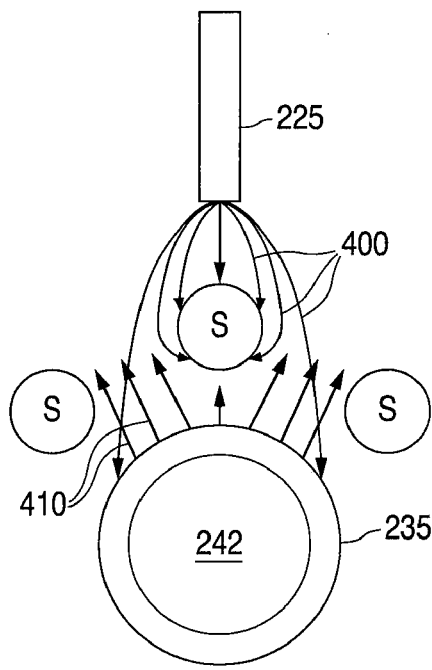
FIG. 7 is a magnified cross section of a stent strut with no wrap around effect.
Figure 8:
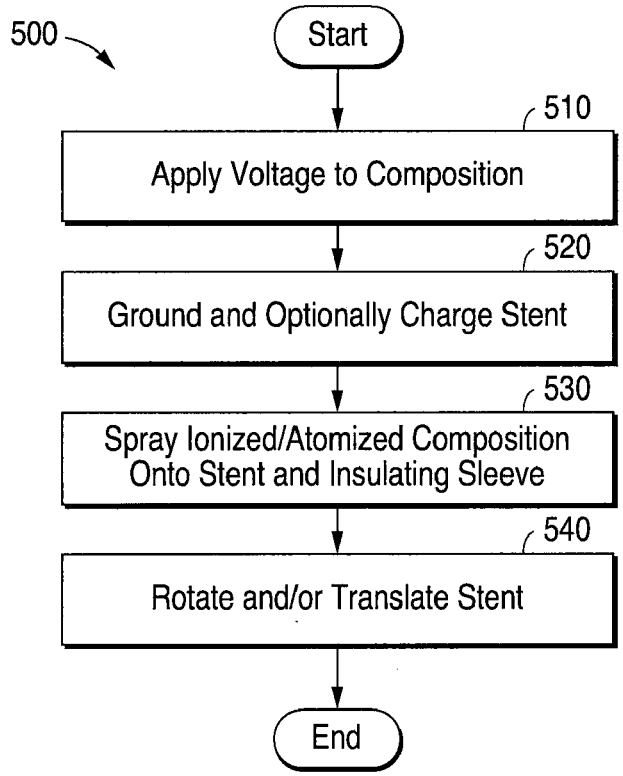
FIG. 8 is a flowchart illustrating a method of electrostatic spray coating.

FIG. 6 is chart illustrating spray regimes as a function of applied voltage and electrode separation. Applied voltage is based on the power source 245 and the high voltage transformer 250. Electrode separation refers to the distance between the stent 100 and the hypotube 225. Ideally, appropriate voltage is applied to the hypotube 225 to enter the fine spray regime, which provides adequate atomization. If inadequate voltage is applied to the hypotube 225, there will not be sufficient atomization, thereby causing the composition to exit the hypotube 225 as a drip instead of as the atomized spray 230. Too much voltage on the other hand will lead to a sputtering regime in which the composition exits the hypotube 225 in spurts instead of as the atomized spray 230.

FIG. 7 is a diagram illustrating a magnified cross section of a portion of the electrostatic spray coating system 200. Electric field lines 400 extend downward from the hypotube 225 towards struts S of the stent 100. In addition, the electric field lines 400 wrap around the struts S and can extend towards the insulating sleeve 235. During a spray coating process, initially, the spray 230 follows the electric field lines 400 coating the insulating sleeve 235, the abluminal surface of the stent 100, and slightly coating the luminal surface of the stent 100.

During the initial stages of the spray coating process, a charge of the same polarity as the spray 230 builds up on the insulating sleeve 235, thereby generating electric field lines 410 that counteract the electric field lines 400. The electric field lines 410 extend outward from the insulating sleeve 235 and prevent and repel the spray 230 from further coating the luminal surface of the stent 100. Accordingly, coating of the luminal surface of the stent 100 is substantially limited. In an embodiment of the invention, the insulating sleeve 235 (or coating or nonconductive mandrel parts) can come pre-charged so that the electric field lines 410 are generated prior to the beginning of the spray coating process, thereby preventing or reducing any coating of the luminal surface of the stent 100 with the spray 230. The insulating sleeve 235 (or coating or nonconductive mandrel parts) can be pre-charged by, for example, spraying the sleeve 235 or coating before loading the stent 100 onto the system 200.

In some embodiments, during the spray coating process, the stent 100 is in electrical contact with the stent mandrel fixture 240 and is grounded and can be supplied with a charge opposite the charge of the spray 230. The fixture 240 can be supplied with an opposite charge by electrically coupling the fixture 240 to the power source 245, which supplies a first charge to the spray 230 and an opposite charge to the fixture 240. This difference in polarity increases the attraction of the spray 230 to the stent 100, therefore increasing coating of the stent 100. This difference in polarity can also compensate for misalignment of the hypotube 225 with the stent 100, which is a critical issue during the conventional applications of a composition to a drug releasing stent. Specifically, the polarity difference will pull the spray 230 towards the stent 100 even if the stent 100 is not positioned directly beneath the hypotube 225.

FIG. 8 is a flowchart illustrating a method 500 of electrostatic spray coating. In an embodiment of the invention, the system 200 executes the method 500. First, a high voltage is applied (510) to the composition as it travels through the hypotube 225, which ionizes and atomizes the composition so that it can be ejected as atomized ionized spray 230. The stent 100 is then grounded and optionally charged (520) so that there is a charge or polarity differential between the spray 230 and the stent 100 so that the stent 100 attracts the spray 230. The ionized atomized composition is then sprayed (530) onto the stent 100 and the insulating sleeve 235, thereby forming a charge on the sleeve 235 so that any additional spray 230 is repelled from the sleeve 235 and therefore the luminal surface of the stent 100. In an alternative embodiment, the sleeve 235 may be pre-charged (e.g., by spraying the sleeve 235 before loading the stent 100 onto the mandrel fixture) and so the spraying (530) only covers the abluminal surface of the stent 100. The stent 100 is also rotated and translated (540) during the spraying (530) so that the entire abluminal surface of the stent 100 can be coated. The method 500 then ends.

It will be appreciated by one of ordinary skill in the art that the applying (510), grounding/charging (520), spraying (530), and rotating/translating (540) can occur in any order and is not limited to the order disclosed above. Further, the applying (510), grounding/charging (520), spraying (530), and rotating/translating (540) can occur substantially simultaneously instead of sequentially.

The following examples are provided:

EXAMPLE 1

In an example spray process, parameters according to Table I were used. The composition comprised 2% weight Poly(DL-Lactide) in 80/20 acetone/cyclohexanone solvent mixture. A blue dye was added to the formulation to replace the drug and to provide the contrast. The polymer to dye ratio was 1 to 1. The stent mandrel fixture was grounded through a wire with an alligator clip. The spray cycle was programmed for 10-seconds spray and 10-seconds drying cycle. The total coating weight was 630 μg. The stent was an 18 mm Vision stent available from Guidant. A pellethane tube was used between the stent and the mandrel to create the repulsive force.

TABLE I

| | | |
|---|---|---|
| Mandrel Spin Rate | 150 | RPM |
| Start Position | 25 | mm |
| End Position | 54 | mm |
| Dry Position | 120 | mm |
| Drying Nozzle Temperature Set Point | 60° | C. |
| Drying Air Pressure | 23 | PSI |
| Electrode Separation | 20-25 | mm |
| Applied Voltage | 4-10 | KV |

EXAMPLE 2

Cleaned 18 mm Vision stents (Guidant Corp.) were first primered with 2 wt % of poly(butyl methacrylate) solution using a modified N1537 spray coater and the coating weight was in the range of 75 to 90 µg. The primered stents were mounted on a metallic mandrel with one additional metallic collet, which was used to support the stent and to provide the contact points for ground. The mandrel was grounded through a wire with an alligator clip. SOLEF formulation was used for the drug coat of everolimus (190 µg dose with polymer to drug ration of 3.12 to 1). SOLEF is a trade name of poly(vinylidene fluoride-co-hexafluoropropene) available from Solvay Fluoropolymers, Inc. of Houston, Tex. The deposited rate per spray cycle was controlled in the range of 15 to 20 µg. The spray cycle was programmed for 10-seconds spray and 10-seconds dry cycle. The drying temperature was set at 60 deg. C. and the air pressure was set at 23 psi. A post oven bake at 50 deg. C. for 1 hour was conducted and the coating weight on the 18 mm Vision stents were targeted in the range of 785 µg to 835 µg.

EXAMPLE 3

A bare metal stent was mounted over a metallic spray mandrel. The mandrel was grounded through a wire with an alligator clip. D, L-PLA formulation, 80/20 acetone to cyclohexanone with 1:1 polymer to everolimus ratio, was used for the drug coating. The deposit rate per spray cycle was controlled in the range of 70 to 80 µg. The voltage was controlled between 6 to 8 KV. The spray cycle was programmed for 10-seconds spray and 10-seconds dry cycle. The dry temperature was set at 60 deg. C. and the air pressure was set at 23 psi. A post bake at 50 deg. C. for 1 hour was conducted and the coating weight on the 18 mm stent was targeted in range of 630 µg to 730 µg.

While particular embodiments of the present invention have been shown and described, it will be obvious to one of ordinary skill in the art that changes and modifications can be made without departing from this invention in its broader aspects. For example, after application of the coating to the abluminal surface of the stent 100 as described above, the luminal surface of the stent 100 can be coated with a different coating via spray coating, electroplating or other technique. Therefore, the appended claims are to encompass within their scope all such changes and modifications as fall within the true spirit and scope of this invention.

What is claimed is:

1. A method for spraying an outer surface of a stent with a coating substance, comprising the steps of:
providing a stent in conductive contact with a first mandrel component supporting the stent and applying a charge to the stent and/or grounding the stent, wherein an end portion of the first mandrel component supports the stent, and the end portion includes a non-conductive sleeve, a non-conductive coating or the end portion is made from a non-conductive material;
disposing a second mandrel component at least partially within a bore of the stent, the second mandrel component being spaced from the walls of the bore, the second mandrel component including an outermost surface exposed to at least a portion of the walls of the bore and being made from a nonconductive material or being coated with a nonconductive material;
charging a coating substance; and
spraying the stent with the charged coating substance.

2. The method of claim 1, wherein the second mandrel component includes an outermost surface exposed to all of the walls of the bore.

3. The method of claim 1, wherein the stent has a first and second end being supported by respective first and second end portions of the first mandrel component, wherein the first end portion is made from a non-conductive material, or is insulated with a non-conductive sleeve or a coating and the second end portion provides the conductive contact between the first mandrel and stent.

4. The method of claim 1, wherein the end portion includes a conductive part for forming the conductive contact with the stent and a segment comprising a non-conductive sleeve, a non-conductive coating or a non-conductive material.

5. The method of claim 1, wherein the non-conductive material or coating is patterned so as to provide areas where a conductive material of the second mandrel is exposed to the stent so as to selectively coat designated areas of an inner surface of the stent.

6. A method for spraying an outer surface of a stent with a coating substance, comprising the steps of:
providing a stent in conductive contact with a first mandrel component supporting the stent and applying a charge to the stent and/or grounding the stent;
disposing a second mandrel component at least partially within a bore of the stent, the second mandrel component being spaced from the walls of the bore, the second mandrel component including an outermost surface exposed to at least a portion of the walls of the bore and being made from a nonconductive material or being coated with a nonconductive material;
charging a coating substance; and
spraying the stent with the charged coating substance;
wherein the second mandrel component includes an outermost surface exposed to only a portion of the walls of the bore.

7. The method of claim 6, wherein the outermost surface of the second mandrel extends beyond the length of the stent.

8. A method for applying a composition to a stent, comprising the steps of:
applying a charge to the stent and/or grounding the stent;
ionizing a composition;
disposing a mandrel component within a bore of the stent, the mandrel component having an outermost surface spaced from and exposed to a luminal surface of the stent and an electric field extending from the outermost surface and having the same polarity as the ionized composition; and
spraying the stent with the ionized composition including limiting or preventing composition from coating the luminal surface of the stent by the electric field repelling the ionized composition;
wherein the stent is supported at only one end by the mandrel component.

9. The method of claim 8, wherein the mandrel component carries the same charge as the ionized composition.

10. The method of claim 8, wherein the stent is rotated and/or translated as the stent is sprayed with the ionized composition.

11. The method of claim 8, wherein the stent is coupled to a power source, further including using the power source to maintain a neutral charge on the stent or maintain a charge opposite of the ionized composition during the spraying step.

12. The method of claim 8, further including the step of applying a voltage sufficient to both atomize and ionize the composition.

13. The method of claim 8, further including the step of atomizing the composition using an air-assisted atomization nozzle and power source.

14. The method of claim 8, wherein the stent is crimped or friction fit to the mandrel component.

15. A method for applying a composition to a stent, comprising the steps of:
- applying a charge to the stent and/or grounding the stent;
- ionizing a composition;
- disposing a first mandrel component within a bore of the stent, the first mandrel component having an outermost surface spaced from and exposed to a luminal surface of the stent and an electric field extending from the outermost surface and having the same polarity as the ionized composition;
- spraying the stent with the ionized composition including limiting or preventing composition from coating the luminal surface of the stent by the electric field repelling the ionized composition; and
- disposing a second mandrel component at least partially within the bore of the stent;
- wherein the second mandrel component is made from a nonconductive material or coated with a nonconductive material, so that the electric field extending from the outermost surface is formed from ionized composition collected on the outermost surface.

16. A method for applying a composition to a stent, comprising the steps of:
- applying a charge to the stent and/or grounding the stent;
- ionizing a composition;
- disposing a first mandrel component within a bore of the stent, the first mandrel component having an outermost surface spaced from and exposed to a luminal surface of the stent and an electric field extending from the outermost surface and having the same polarity as the ionized composition;
- spraying the stent with the ionized composition including limiting or preventing composition from coating the luminal surface of the stent by the electric field repelling the ionized composition; and
- spraying the mandrel component with the ionized composition before disposing the mandrel component within the bore of the stent.

* * * * *